United States Patent [19]

Torossian et al.

[11] 4,177,268

[45] Dec. 4, 1979

[54] METHOD OF ALLEVIATING INFLAMMATION BY ADMINISTRATION OF DEXAMETHASONE DERIVATIVES

[75] Inventors: Dieran R. Torossian, Bourg-la-Reine; Gilbert G. Aubard; Jacky M. Legeai, both of Palaiseau, all of France

[73] Assignee: Jouveinal S.A., Cachan, France

[21] Appl. No.: 756,601

[22] Filed: Jan. 4, 1977

Related U.S. Application Data

[63] Continuation-in-part of Ser. No. 473,388, May 28, 1974, Pat. No. 4,014,909.

[30] Foreign Application Priority Data

May 30, 1973 [FR] France .................... 73 19734

[51] Int. Cl.² .................... A61K 31/56; C07J 7/00; C07J 31/00
[52] U.S. Cl. .................... 424/243; 260/397.45
[58] Field of Search .................... 424/243; 260/397.45

[56] References Cited

U.S. PATENT DOCUMENTS

| | | | |
|---|---|---|---|
| 2,814,632 | 11/1957 | Nussbaum | 260/397.45 |
| 3,687,942 | 8/1972 | Anner | 260/239.55 |
| 3,803,133 | 4/1974 | Vogt | 260/239.55 D |

FOREIGN PATENT DOCUMENTS

| | | | |
|---|---|---|---|
| 1187M | 3/1962 | France | 260/397.45 |
| 2070077 | 10/1971 | France | 260/397.45 |

*Primary Examiner*—Ethel G. Love
*Attorney, Agent, or Firm*—Charles E. Baxley

[57] ABSTRACT

The present invention relates a method for the alleviation of inflammation which comprises administering to a host a therapeutically effective amount of a dexamethasone derivative of the formula

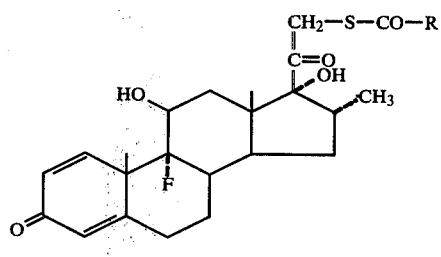

in which R represents an alkyl radical comprising a number of carbons atoms between 4 and 9 or a para-fluoro-phenyl radical.

The product used in this method has a considerable local anti-inflammatory activity.

18 Claims, No Drawings

METHOD OF ALLEVIATING INFLAMMATION BY ADMINISTRATION OF DEXAMETHASONE DERIVATIVES

CROSS REFERENCE

The present application is a continuation in part application of application Ser. No. 473,388, filed May 28, 1974, now U.S. Pat. No. 4,014,909.

BACKGROUND OF INVENTION

The present invention relates a method for the alleviation of inflammation which comprises administering to a host a therapeutically effective amount of a dexamethasone derivative of the formula.

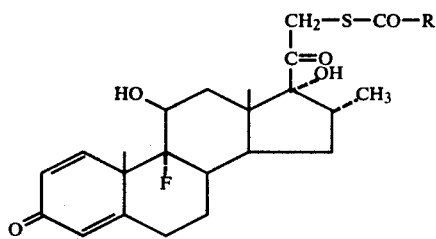

in which R represents an alkyl radical comprises a number of carbons atoms between 4 and 9 or a para-fluorophenyl radical.

The product used in this method has a considerable local anti-inflammatory activity.

Several publications describe the modification of the group 21-hydroxy-methyl of dexamethasone, and more particularly the replacement of the oxygen of this function by sulphur.

Thus, 21-thio-acetate of dexamethasone (French Pat. No. 1187 M) has been proposed as an anti-inflammatory product with a local action and a systemic action, 3 or 4 times as active as prednisolone.

In another French Pat. No. 2.070.077 the 21-thiopivalate of dexamethasone have been quoted as starting material for the synthesis of derivatives of corticoids but no pharmacological or therapeutical activity have been described.

The therapeutic use of corticoids having a systemic action generally gives rise to harmful "secondary effects" (Presse Medicale No. 31,1419–1423, 1970).

These secondary effects comprise mainly: endocrine troubles, sodium retention accompanied by a leakage of potassium, weakening of the defense reactions of the organism, which result in a pro-infection effect, digestive ulcers and disturbances of the glucidic, proteic and lipic metabolisms.

The number and the variety of these secondary effects necessitate a certain prudence and careful supervision during the use of these products.

The present invention has for its object to find a remedy for these disadvantages.

STATEMENT OF INVENTION

It has been found that, in a surprising manner, the structures forming the object of the present invention comprising a thio-alkanoic group of high molecular weight, possess a considerable local anti-inflammatory activity.

Thus, local anti-inflammatory activity of certain substances is 100 to 200 times more active than prednisolone without any important change in their systemic activity. The therapeutic doses thus remain very remote from those capable of causing the appearance of the secondary effects previously described.

In consequence, these substances are therapeutic agents having a very high safety in use, which find their application in the local treatment of inflammatory affections, such as the following:

Cutaneous illnesses and mucous illnesses that can be treated by corticoids;

Auto-rhino-laryngological and ophthalmological illnesses of an inflammatory and/or allergic nature;

Low digestive inflammations such as colities, recto-colities, and recto-sigmoiditis;

Collagen troubles, articular and rhumatismal illnesses;

Asthma, emphysema and respiratory fibrosis.

The dexamethasone derivatives used in this invention are known or can, if they are new, be obtained in a manner which is in itself known. (U.S. Pat. No. 2,814,632 for example).

DESCRIPTION OF PREFERRED EMBODIMENTS

The manufacture of some dexamethasone derivatives are described in more detail in the examples which follows:

EXAMPLE 1

DIHYDROXY-11β,17α THIOL-21 DIOXO-3.20 FLUORO-9α METHYL-16α PREGNADIENE-1.4-21-PIVALATE (JO 1008)

In a three necked round bottomed flask of one liter there is prepared sodium S-thio-pivalate starting with 10.35 grams of S-thiopivalic acid. (87.6 mmoles) and 27.3 cu.cm. of sodium methylate solution 3.21 M (87.6 mmols) in 150 cu.cm. of anhydrous acetone.

There is then introduced rapidly 3.4 grams of dihydroxy-11β,17α iodo-21 dioxo-3.20 fluoro-9α methyl-16α pregnadiene-1.4 (6.76 mmols) in solution in 200 cu.cm. of anhydrous acetone.

After two hours at the reflux of acetone, the solvent is eliminated by distillation under vacuum. The yellow oily residue is poured into 100 cu.cm. of water, filtered and dried under vacuum at 40° C. There are obtained 2.6 grams of crude product which are purified by crystallization from methanol; weight: 2.39 grams; yield=71.8%.

Analysis: $C_{27}H_{37}FO_5S$: Calculated %: C 65.82, H 7.57, F 3.86, S 6.51: Found %: C 65.95, H 7.63, F 3.87, S 6.59.

Physical characteristics:
M.P.=240°–245° C.
$(\alpha)_D^{20}=+92°$, (dioxanne; c=1%)
λ max. (methanol) at 236.5 nm, $\log_{10} \epsilon = 4.270$
Main absorptions of infra-red spectrum (KBr pellet): 1715, 1660, 1610, 1455, 1140, 980, 950, 930, 900 and 710 $cm^{-1}$

EXAMPLE 2

DIHYDROXY-11β,17α THIOL-21 DIOXO-3.20 FLUORO-9α METHYL-16α PREGNADIENE-1.4-21 HEPTANOATE (JO 1010)

The reaction is carried out as described in Example 1 starting with 12.81 grams of S-heptanethioic acid (87,6 mmols) on the one hand; and 3.4 grams of dihydroxy- 11β,17α iodo-21 dioxo-3.20 fluoro-9α methyl-16α-pregnadiene-1.4 (6,76 mmols) on the other hand.

After reaction and evaporation of the acetone, the residue is treated with 800 cu.cm. of water and the suspension is extracted by three times 100 cu.cm. of chloroform. The combined organic phases are dried and there are obtained 4.6 grams of an oily residue after evaporation of the chloroform under vacuum.

The residue is first purified by column chromatography on 70 grams of Florisil, tradename for a mixture of magnesium oxide and silicon oxide (15–85 w/w) 60–100 mesh. After the passage of hexane and then benzene, the elution by chloroform permits the collection of 3.2 grams of product which are crystallized from an ethanol-hexane mixture; weight: 1.25 grams; yield: 35.5%.

Analysis: $C_{29}H_{41}FO_5S$: Calculated %: C 66.89, H 7.94, F 3.65, S 6.16: Found %: C 67.19, H 8.14, F 3.70, S. 6.22.

Physical characteristics:
M.P.: 145°–150° C.
$(\alpha)_D^{20} = +82°$, (dioxanne: c=1.4%)
λ max. (methanol) at 236.5 nm, $\log_{10} \epsilon = 4.294$
Main absorptions of infra-red spectrum (KBr pellet): 1710, 1660, 1610, 1455, 1140, 980, 950, 930, 900 and 710 cm$^{-1}$

EXAMPLE 3

DIHYDROXY-11β,17α THIO-21 DIOXO-3.20 FLUORO-9α METHYL-16α PREGNADIENE-1.4-21 DECANOATE (JO 1052)

Carrying out the operation under the same conditions as in EXAMPLE 1, from 4,39 grams of S-decanethioic acid (23,3 mmols), 6,1 cu.cm. of sodium methylate solution 3,8 N (23,3 mmols) and 9,75 grams of dihydroxy-11β,17α iodo-21 dioxo-3,20 fluoro-9α methyl-16α pregnadiene-1,4 (19,4 mmols), there are obtained after treatment and crystallisation from methanol 6,1 grams of white crystals; yield=51,5%.

Analysis: $C_{32}H_{47}FO_5S$: Calculated %: C 68,29, H 8,42, F 3,65, S 6,16: Found %: C 68.36, H 8,38, F 5,90, S 3,34.

Physical characteristics:
M.P.=145°–148° C.
$(\alpha)_D^{20} = +87°$, (dioxanne, c=1%)
λ max. (methanol) at 237 nm, $\log_{10} \epsilon = 5,28$
Main absorptions of infra-red spectrum (KBr pellet): 2920, 2850, 1660, 1610, 1600, et 895 cm$^{-1}$ By proceeding in the manner of EXAMPLE 1, but with S-thioalkanoics acids indicated in Column 1 below the thio esters of Column 2 are obtained.

| COLUMN 1 | COLUMN 2 |
| --- | --- |
| S-pentanethioic acid | dihydroxy-11β, 17α thiol-21 dioxo-3.20 fluoro-9α methyl-16α pregnadiene-1.4-21 pentanoate |
| S-methyl-2 butanethioic acid | dihydroxy-11β, 17α thiol-21 dioxo-3.20 fluoro-9α methyl-16α pregnadiene-1.4-21 methyl-2 butanoate |
| S - methyl-3 butanethioic acid | dihydroxy-11β, 17α thiol-21 dioxo-3.20 fluoro-9α methyl-16α pregnadiene-1.4-21 methyl-3 butanoate |
| S-hexanethioic acid | dihydroxy-11β, 17α thiol-21 dioxo-3.20 fluoro-9α methyl-16α pregnadiene-1.4-21 hexanoate |
| S-methyl-4 pentanethioic acid | dihydroxy-11β, 17α thiol-21 dioxo-3.20 fluoro-9α methyl-16α pregnadiene-1.4-21 methyl 4-pentanoate |
| S - dimethyl-3,3 butanethioic acid | dihydroxy 11β,17α thiol-21 dioxo-3.20 fluoro-9α methyl-16α pregnadiene-1.4-21 dimethyl-3.3 butanoate |
| S-ethyl-2 butanethioic acid | dihydroxy 11β, 17α thiol-21 dioxo-3.20 fluoro-9α methyl-16αpregnadiene-1.4-21 ethyl-2 butanoate |
| S-octanethioic acid | dihydroxy 11β, 17α thiol-21 dioxo-3.20 fluoro-9α methyl-16α pregnadiene-1.4-21 octanoate |
| S-ethyl-2 hexanethioic acid | dihydroxy 11β, 17α thiol-21 dioxo-3.20 fluoro-9α methyl-16α pregnadiene-1.4-21 ethyl-2 hexanoate |
| S-nonanethioic acid | dihydroxy 11β, 17α thiol-21 dioxo-3.20 fluoro-9α methyl-16α pregnadiene-1.4-21 nonanoate |

EXAMPLE 4

DIHYDROXY-11β,17α THIOL-21 DIOXO-3.20 FLUORO-9α METHYL-16α PREGNADIENE-1.4-21 p. FLUORO BENZOATE (JO 1013)

The reaction is carried out according to Example 1, starting from 13.68 grams S-p. fluoro-thiobenzoic acid (87.6 mmols), 24.4 cu.cm. of sodium methylate solution 3.6 M (87.6 mmols) and 3.4 grams of dihydroxy-11β,17α iodo-21 dioxo-3.20 fluoro-9α methyl-16α pregnadiene-1.4 (6.76 mmols).

After reaction and evaporation of the solvent, the residue is treated with 800 cu.cm. of water and the insoluble is filtered and dried under vacuum—weight: 4.6 grams.

The crude product is purified by column chromatography on Florisil 60–100 mesh (80 grams). Elution by hexane and then by benzene eliminates the coloured products, and then elution by a benzene-chloroform mixture 1–3 (v/v) give 0.9 grams of residue which is crystallised from an ethanol-hexane mixture. Weight: 0.45 grams; yield: 12.5%.

Analysis: $C_{29}H_{32}F_2O_5S$: Calculated %: C 65.64, H 6.08, F 7.16, S 6.04; Found %: C 65.33, H 6.24, F 7.04, S 5.92.

Physical characteristics:
M.P.=205°–210° C.
$(\alpha)_D^{20} = +265°$, (dioxanne c=0.5%)
λ max. (methanol) at 236.5 nm, $\log_{10} \epsilon = 4.516$
Main absorptions of infra-red spectrum (KBr pellet): 1720, 1660, 1598, 1500, 1220, 1200, 1160, 920, 890, 840

PHARMACOLOGICAL STUDY

There will now be described the tests which have enabled the determination of the pharmaco-dynamic properties of the esters of the 21-thiols steroids according to the invention.

ANTI-INFLAMMATORY ACTIVITY

The experimental local anti-inflammatory activity of the compounds presented was estimated in rats by their anti-proliferative (anti-granulomatous) action, and for one of these, by its anti-arthritic activity.

(a) Anti-proliferative activity

The anti-proliferative (anti-granulomatous) activity has been brought into evidence by means of a test, the principle of which is as follows.

The introduction of a foreign body into an organism produces a set of inflammatory reactions which results, in the chronic stage, in the formation of a defence granuloma around the foreign body. The proliferation of this granuloma is eliminated or attenuated by anti-inflammatory agents.

The technique employed is very similar to that described by Winter and Porter (J. Am. Pharm. Ass. 46/9. 515 1957) with rats.

Homogeneous groups of 10 male adult rats of the Wistar Strain were used, distributed at random and having weights comprised between 180 and 200 grams.

The implants or pellets were prepared from rolls of dental cotton; the weight of the pellets was between 35 and 40 mg.

Immediately before their introduction, the pellets were soaked with an antibiotic solution (0.1 ml. of a solution of penecillin G and streptomycin containing 200 000 UI of penicillin G and 0.1 gram of streptomycin sulphate per cc.).

Each animal received two pellets in the sub-cutaneous dorsal tissue on each side of the spinal column, at the costo-lumbar angle, under light anaesthesia with ether. The day of the operation and for three days after, the animals received by sub-cutaneous injection, 0.1 ml. of the antibiotic solution in the caudal region.

Six days after the introduction, the animals were killed by inhalation of chloroform and the granulomae were extracted and weighed, (wet and dry), and then the initial weights of the cotton pellets were substracted from the total weight.

Certain non-sulphured steroids causing a large increase in protein catabolism which can influence the formation of the granuloma independently of their anti-inflammatory action, the weights of the granulomae were expressed as a percentage of the body weight (technique proposed by G. Dipasquale and A. Meli: J. Pharm. Pharmacol. (1965), 17, 367–382) and the antiproliferative effect of the various compounds as a percentage inhibition with respect to the reference granulomae. The $ED_{50}$ were calculated by transferring the results on semi-logarithmic paper.

(a) Local anti-inflammatory activity

For this study, the products to be tested were dissolved in chloroform or in dimethylsuphoxide (DMSO) and the solutions obtained, deposited on the pellets at a volume of 0.2 ml per pellet. The solvent was then evaporated under high vacuum at ambient temperature, the complete elimination of the solvent being checked by weighing the pellets. "Reference" pellets, soaked with the solvent alone, were treated in the same manner.

(b) Anti-arthritic activity

The anti-arthritic activity was brought out by means of a test, the principle of which is as follows:

This test was carried out following a method derived from that described by Foldi-Borcsok and Coll. (Arzneimittel Forschung 21, 2025–2030, 1971).

The injection of kaolin in the tibio-metatarsal joint of the rat causes an inflammation which develops in two successive phases:
 an acute phase characterized by an oedema of the joint;
 a chronic phase which follows, characterized by the proliferation of an inflammatory granuloma.

The intensity of the inflammatory reaction is estimated following the width of the articulation.

Male rats of Wistar stock were utilized, the initial weight of which was between 180 and 200 grams. Each group comprised ten animals taken at random, in which the width of the right-paw tibio-metatarsal joint was measured to the nearest 1/20th of a millimeter.

All the animals received 0.05 ml. of suspension of kaolin at 10% in a 0.9% physiological solution by intra-articular injection in the right-paw tibio-metatarsal joint.

Eighteen hours after this injection, the width of the joint was measured (initial inflammation) and there was then carried out an intra-articular injection of the products under study, in suspension in 0.5% carboxy-methyl-cellulose at a volume of 0.05 ml. The animals belonging to the control lot received 0.05 ml of the vehicle by the same method.

Twenty-four hours after this last injection, the width of the joint treated was again measured and then daily for 9 or 10 days, according to the evolution of the animals of the control group.

The variation of width of the joints treated, representing the anti-arthritic activity of the products under study, were expressed as a percentage of the initial inflammation according to the formula:

$$\text{Anti-arthritic activity on the } N\text{th day} = \frac{\Delta_1 - \Delta_n}{\Delta_1} \times 100$$

in which:
 $\Delta_1$=increase in width of the joint with respect to its initial width, during the initial inflammation;
 $\Delta_n$=increase in width of the joint with respect to its initial width, on the day considered.

The calculations were carried out by using the averages of the individual results of each lot.

SYSTEMIC EFFECTS

The systemic effects of the compounds according to the invention were evaluated through the intermediary of their thymolytic activity and for some of these, their possible influence on the glucidic metabolism, the hydro-mineral equilibrium, the weight increase, the endocrine glands and the genital tractus was examined and also a possible ulcerogenic effect.

(c) Thymolytic effect

The thymolytic effects have been examined by means of a test, the principle of which is as follows:

The repeated administration of a gluco-corticoid having a systemic activity causes an involution of the defence system of the organism, of which two organs belong to the reticuloendothelial system, the spleen and the thymus, this latter being the most sensitive to this action, especially with young animals. The thymic involution is estimated by weighing.

The thymolytic effects was studied by two routes:
1. Sub-cutaneous route
2. Oral route For this study, the various products were injected daily by the oral or the sub-cutaneous route for four days, to young male rats of Wistar-strain, the initial weight of which was between 45 and 55 grams, distributed at random by groups of ten.

The products under study were administered at a volume of 0.2 ml. per animal for both routes, in suspension in:
 Carboxy-methyl-cellulose at 0.5% for sub-cutaneous injection;
 Gum arabic at 5% for the oral route.

The animals of the control groups received the same volume of the corresponding vehicle.

Ninety-six hours after the first administration, the animals were killed, the thymus glands being taken and weighed immediately.

For each animal, the weight of the thymus has been brought to 100 grams of body weight. The thymolytic activity of the products under study was then expressed as a percentage of regression of the thymus with respect to the animals of the control group and the $ED_{50}$ of each product tested was estimated by transferring the percentage inhibition obtained for each dose on semilogarithmic paper.

RESULTS OF PHARMACOLOGICAL STUDY

Now there will be described the results of pharmacological study:

Anti-inflammatory activity (a) Local anti-proliferative activity

The obtained $ED_{50}$ for each of the presented compounds and their reference steroids are indicated in the TABLE I.

TABLE I

| TREATMENT | WET WEIGHT OF PELLET | DRY WEIGHT OF PELLET |
|---|---|---|
| Dexamethasone base | $ED_{50}$ = 1 mg/pellet | $ED_{50}$ = 1 mg/pellet |
| Prednisolone base | $ED_{50}$ = 4 mg/pellet | $ED_{50}$ = 2 mg/pellet |
| JO 1008 | $ED_{50}$ = 0,045 mg/pellet | $ED_{50}$ = 0,024 mg/pellet |
| JO 1010 | $ED_{50}$ = 0,017 mg/pellet | $ED_{50} \leq$ = 0,017 mg/pellet |
| JO 1013 | $ED_{50}$ = 0,07 mg/pellet | $ED_{50}$ = 0,047 mg/pellet |

This chart shows that, when administered by local route, the compounds according to the invention are active in doses much smaller than those needed with reference steroids.

(b) Anti-arthritic activity

The results reported in the TABLE II represent the anti-arthritic activity of one of the presented compounds, estimated from the diminution in the width of the joint (as a percentage of the initial inflammation), 24 hours and 120 hours after the injection.

TABLE II

| | DOSE | 24 HOURS | 120 HOURS |
|---|---|---|---|
| Dexamethasone base | 0,100 mg | −78,8% | −51,3% |
| Prednisolone base | 1,000 mg | −57,7% | −1,9% |
| JO 1008 | 0,126 mg | −64,7% | 90,8% |

When administered by local route, compound JO 1008 exerts for 24 hours an antiarthritic activity similar to that of reference steroids. However this effect remains at its maximum level for 120 hours whereas, at the end of the same 120 hour period, the effect of the reference steroids has significantly dropped, if not disappeared.

(c) Thymolytic activity

The $ED_{50}$ obtained for each compounds and their reference steroids are indicated in the TABLE III.

TABLE III

| TREATMENT | ORAL ROUTE | SUB-CUTANEOUS ROUTE |
|---|---|---|
| Dexamethasone base | $ED_{50}$ = 0,013 mg | $ED_{50}$ = 0,02 mg |
| Prednisolone base | $ED_{50}$ = 0,34 mg | $ED_{50}$ = 0,84 mg |
| JO 1008 | $ED_{50}$ = 0,160 mg | $ED_{50}$ = 0,80 mg |
| JO 1010 | $ED_{50}$ = 0,288 mg | $ED_{50}$ = 0,40 mg |
| JO 1013 | $ED_{50}$ = 0,184 mg | $ED_{50}$ = 0,80 mg |

When administered by systemic route, the activity of the compounds accorging to the invention is less than that of dexamethasone base and similar to that of prednisolone base.

The present invention can be carried out by conventional methods, the products being incorporated in vehicules compatible with administration. Thus they can be presented in the form of solution or suspension leading to conventional presentations such as lotions, spray, car, ophtalmic or nasal drops, mouthwash, injectable, pastille, ointments, creams, oral or rectal suspension, powder, etc.

The product concentration will be between 0.005 to 5% and will advantageously be established at 0.01% for topical application, and at 1% for oral or parenteral administration.

EXAMPLES

The following examples are given to permit a better understanding of the invention, without, however, limiting its scope:

AQUEOUS SUSPENSION (for nasal drops, ear drops, or rectal administration)

Formulation

Each 10 g of "JO 1008—Nasal drops" preparation contains:

| | |
|---|---|
| JO 1008 | 0,010 g |
| N-cetylpyridinium chloride | 0,002 g |
| Benzyl alcohol | 0,050 g |
| Sodium chloride | 0,075 g |
| Sodium biphosphate, 2 $H_2O$ | 0,015 g |
| Water to make | 10 g |

In a glass vessel, put enough water to dissolve N-cetylpyridinium chloride, benzyl alcohol, sodium chloride, sodium biphosphate. Add finely pulverized JO 1008. Stir until completely dispersed. Bring to total volume with water. Distribute into suitable receptacles.

This formulation can be presented with or without antibiotic as neomycin sulfate or with vasoconstrictor as naphazoline.

AQUEOUS STERILE SUSPENSION (for parenteral administration and ophtalmic preparation)

Formulation

Each 10 g of "JO 1008 ophtalmic" preparation contains:

| | |
|---|---|
| JO 1008 | 0,010 g |
| Neomycin sulfate | 0,035 g (base) |
| Polymyxin B sulfate | 60,000 USP units |
| Polysorbate 20 | 0,005 g |
| Sodium chloride | 0,085 g |
| Benzalkonium chloride | 0.0004 g |

| | |
|---|---|
| Hydroxypropyl Methylcellulose N.F. | 0,050 g |
| Water to make | 10 g |

In a sterile glass vessel, put a sterilized by autoclaving aqueous solution of 5% polysorbate 20, a sterilized by autoclaving aqueous solution of 2% hydroxypropyl methylcellulose, a sterilized by filtration aqueous solution of benzalkonium chloride, sodium chloride, neomycin sulfate and polymyxin sulfate.

Aseptically disperse JO 1008 sterilized with ethylene oxide. Bring to total volume with sterile distilled water. Distribute into suitable receptacles.

This formulation can be presented with or without antibiotic or antiseptic.

MOUTHWASH

Formulation

Each 100 g of "JO 1008 mouthwash" preparation contains:

| | |
|---|---|
| JO 1008 | 0,02 g |
| Alcohol 95$^c$ | 56,40 g |
| Saccharin | 0,25 g |
| Menthol | 0,10 g |
| WATER Q.S.P | 100 g |

In a stainless steel vessel, put alcohol and add saccharin, menthol and JO 1008. Stirr until completely dissolved. Bring to total volume with water. Distribute into suitable receptacles.

This formulation can be presented with or without antibiotic or antiseptic.

PASTILLE

Formulation

Each pastille of JO 1008 contains:

| | |
|---|---|
| JO 1008 | 0,0001 g |
| Gelatine | 0,012 g |
| Glucose | 0,015 g |
| Magnesium stearate | 0,015 g |
| Saccharose to make | 1 g |

In a powder mixer, put saccharose and JO 1008, add while stirring an aqueous solution of gelatine and glucose. The wet granulation is forced through a screen. Moist material is placed in drying cabinet. After drying, the granulation is reduced in particle size by passing it through a smaller mesh screen. Add magnesium stearate and compress with a suitable machine. Distribute then in boxes.

This formulation can be presented with or without antibiotic or antiseptic.

AEROSOLS

Formulation

Each 10 ml of aerosol formulation spray contains:

| | |
|---|---|
| JO 1008 | 0,004 g |
| Saccharin | 0,004 g |
| Isopropyl myristate | 2,5 g |
| Dichlorodifluoromethane | 9,5 g |

In a stainless steel vessel, put isopropyl myristate and while stirring add saccharin and JO 1008.

Distribute into a glass vessel for spray, put a valve and due packaging with the propellant into suitable machine.

This formulation can be presented with or without bronchodilatator.

POWDER (Powder paper)

Formulation

Each small sachet of "JO 1008 powder" contains:

| | |
|---|---|
| JO 1008 | 0,002 g |
| Polyvinylpyrrolidone | 0,050 g |
| Polysorbate 80 | 0,004 g |
| Glucose to make | 2 g |

In a powder mixer, put glucose and JO 1008. Add while stirring an alcoholic solution of polyvinylpyrrolidone and polysorbate 80. The wet granulation is forced through a screen. Moist material is placed in drying cabinet. After drying, the granulation is reduced in particle size by passing it through a small mesh screen. The powder is distributed into suitable sachet (small bag).

CREAM

Formulation

Each 100 g of "JO 1008 cream" contains:

| | |
|---|---|
| JO 1008 | 0,1 g |
| White petrolatum | 25 g |
| Stearyl alcohol | 25 g |
| Propylene glycol | 12 g |
| Sodium laury sulfate | 1 g |
| Propyl paraben | 0,015 g |
| Methyl paraben | 0,025 g |
| Water | 37 g |

Melt the stearyl alcohol and the white petrolatum in a steam bath, and warm about 75° C. Add JO 1008. Add the other ingredients, previously dissolved in the water and warmed to 75° C. and stir the mixture until it congeals. Pack in a suitable receptacle.

This formulation can be presented with or without antibiotic or fungistatic.

OINTMENT

Formulation

Each 100 g of "JO 1008 ointment" contains:

| | |
|---|---|
| JO 1008 | 0,1 g |
| White wax | 5 g |
| White petrolatum | 94,9 g |

Melt the white wax in a suitable dish on a water bath, add the white petrolatum, warm until liquefied, then discontinue the heating, add JO 1008 and stir the mixture until it begins to congeal.

Pack in a suitable receptacle.

This formulation can be presented with or without antibiotic or fungistatic.

We claim:

1. A method for the alleviation of inflammation without causing any noticeable systemic effect which comprises administering to a host a antiinflammatory-effective amount of a dexamethasone derivative of the formula

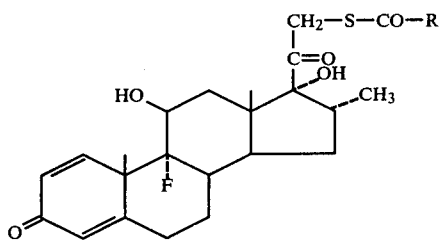

in which R represents an alkyl radical comprising a number of carbon atoms between 4 and 9 or a para-fluoro-phenyl radical.

2. The method of claim 1, which comprises administering dexamethasone 21-thiopivalate as dexamethasone derivative.

3. The method of claim 1, which comprises administering dexamethasone 21-thiopentanoate as dexamethasone derivative.

4. The method of claim 1, which comprises administering dexamethasone 21-thiol-2-methyl-butanoate as dexamethasone derivative.

5. The method of claim 1, which comprises administering dexamethasone 21-thiol-3-methyl-butanoate as dexamethasone derivative.

6. The method of claim 1, which comprises administering dexamethasone 21-thiohexanoate as dexamethasone derivative.

7. The method of claim 1, which comprises administering dexamethasone 21-thiol-4-methyl-pentanoate as dexamethasone derivative.

8. The method of claim 1, which comprises administering dexamethasone 21-thiol-3,3-dimethyl-butanoate as dexamethasone derivative.

9. The method of claim 1, which comprises administering dexamethasone 21-thiol-2-ethyl-butanoate as dexamethasone derivative.

10. The method of claim 1, which comprises administering dexamethasone 21-thiooctanoate as dexamethasone derivative.

11. The method of claim 1, which comprises administering dexamethasone 21-thiol-2-ethyl-hexanoate as dexamethasone derivative.

12. The method of claim 1, which comprises administering dexamethasone 21-thiononanoate as dexamethasone derivative.

13. The method of claim 1, which comprises administering dexamethasone 21-thiodecanoate as dexamethasone derivative.

14. The method of claim 1, which comprises administering dexamethasone 21-p-fluorothiobenzoate as dexamethasone derivative.

15. A pharmaceutical composition comprising 0,005 to 5% of a dexamethasone derivative of the formula

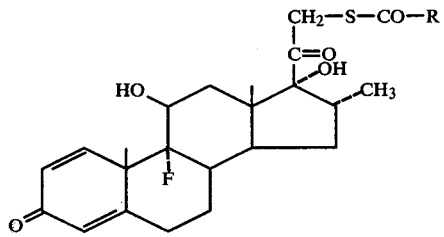

in which R represents an alkylradical having from 4 to 9 carbon atoms or the para-fluoro phenyl radical, and an acceptable pharmaceutical carrier, this composition being presented in the form of a lotion, a spray, ear, ophtalmic or nasal drops, a mouthwash, injectable solutions, pastilles, ointments, creams, oral or rectal suspensions, and the like.

16. The pharmaceutical composition of claim 15 for oral or parenteral administration comprising 1% of dexamethasone derivative.

17. The pharmaceutical composition of claim 15 for topical application, comprising 0,01% of dexamethasone derivative.

18. The 21-p-fluoro-thio-benzoate of dexamethasone.

* * * * *